(12) United States Patent
Wenderow et al.

(10) Patent No.: US 10,271,910 B2
(45) Date of Patent: Apr. 30, 2019

(54) ROBOTIC CATHETER SYSTEM WITH FFR INTEGRATION

(71) Applicant: Corindus, Inc., Waltham, MA (US)

(72) Inventors: Tal Wenderow, Newton, MA (US); Jeffrey Lightcap, Plandome, NY (US)

(73) Assignee: CORINDUS, INC., Waltham, MA (US)

( * ) Notice: Subject to any disclaimer, the term of this patent is extended or adjusted under 35 U.S.C. 154(b) by 512 days.

(21) Appl. No.: 14/885,968

(22) Filed: Oct. 16, 2015

(65) Prior Publication Data

US 2016/0136392 A1 May 19, 2016

Related U.S. Application Data

(60) Provisional application No. 62/064,760, filed on Oct. 16, 2014.

(51) Int. Cl.
*A61B 5/02* (2006.01)
*A61B 34/30* (2016.01)
*A61B 6/12* (2006.01)
*A61B 6/00* (2006.01)
*A61M 25/00* (2006.01)
*A61B 90/00* (2016.01)

(52) U.S. Cl.
CPC ........... *A61B 34/30* (2016.02); *A61B 6/12* (2013.01); *A61B 6/504* (2013.01); *A61B 6/507* (2013.01); *A61B 6/5217* (2013.01); *A61B 6/461* (2013.01); *A61B 2034/301* (2016.02); *A61B 2090/064* (2016.02); *A61M 2025/0002* (2013.01); *A61M 2205/502* (2013.01); *A61M 2230/30* (2013.01)

(58) Field of Classification Search
CPC ............ A61B 5/14532; A61B 5/14503; A61B 5/7225; A61B 5/145; A61B 5/01
See application file for complete search history.

(56) References Cited

U.S. PATENT DOCUMENTS

| 2006/0052700 | A1* | 3/2006 | Svanerudh | A61B 5/0215 600/438 |
| 2009/0221958 | A1* | 9/2009 | Beyar | A61B 90/11 604/95.01 |
| 2012/0041323 | A1* | 2/2012 | Taylor | A61B 5/02007 600/508 |

OTHER PUBLICATIONS

Huo et al; A validated predictive model of coronary fractional flow reserve; Journal of The Royal Society Interface; J.R. Soc. Interface (2012) vol. 9; pp. 1325-1338; Published online Nov. 23, 2011; 14 pages.

* cited by examiner

*Primary Examiner* — Eric J Messersmith
(74) *Attorney, Agent, or Firm* — Rathe Lindenbaum LLP

(57) ABSTRACT

A method includes obtaining a fractional flow reserve (FFR) value over a given distance in a patient's vasculature; providing a display of a region of interest of the patient's vasculature; displaying a graphic on the display of the location of the vasculature having a FFR value outside of a predetermined limit; and robotically positioning a medical elongated device proximate the location.

19 Claims, 2 Drawing Sheets

ROBOTIC CATHETER SYSTEM WITH FFR INTEGRATION

CROSS REFERENCE TO RELATED APPLICATIONS

This application claims priority to U.S. Provisional Patent Application No. 62/064,760 entitled ROBOTIC CATHETER SYSTEM WITH FFR INTEGRATION and filed on Oct. 16, 2014 which is incorporated herein by reference in its entirety.

BACKGROUND OF THE INVENTION

Systems exist for the robotic feeding of percutaneous interventional devices such as guide wires and working catheters into guide catheters and procedures exist for the placement and seating of guide catheters such that their distal ends are adjacent the site of action for the intervention, typically a valve or chamber of the heart or a lesion in a blood vessel such as an artery. The guide catheter is typically placed by manual manipulation of medical personnel and its continued seating after placement assumed or determined by feel. The interventional devices such as guide wires and working catheters may be fed by the operation of robotic controls by medical personnel such as shown in U.S. Pat. No. 7,887,549 incorporated herein by reference in its entirety.

SUMMARY OF THE INVENTION

A robotic catheterization apparatus is used with FFR technology to aid in the selection and/or placement of the stent within a vasculature of a patient.

A method includes obtaining a fractional flow reserve (FFR) value over a given distance in a patient's vasculature; providing a display of a region of interest of the patient's vasculature; displaying a graphic on the display of the location of the vasculature having a FFR value outside of a predetermined limit; and robotically positioning a medical elongated device proximate the location.

An apparatus includes a robotic drive system including a linear drive mechanism. A fractional flow reserve system including a device to calculate a fractional flow (FFR) value over a given distance in a patient's vasculature. A display provides a real time graphic of a patient's vasculature including a display of the FFR value for a region of interest.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Figure 1:
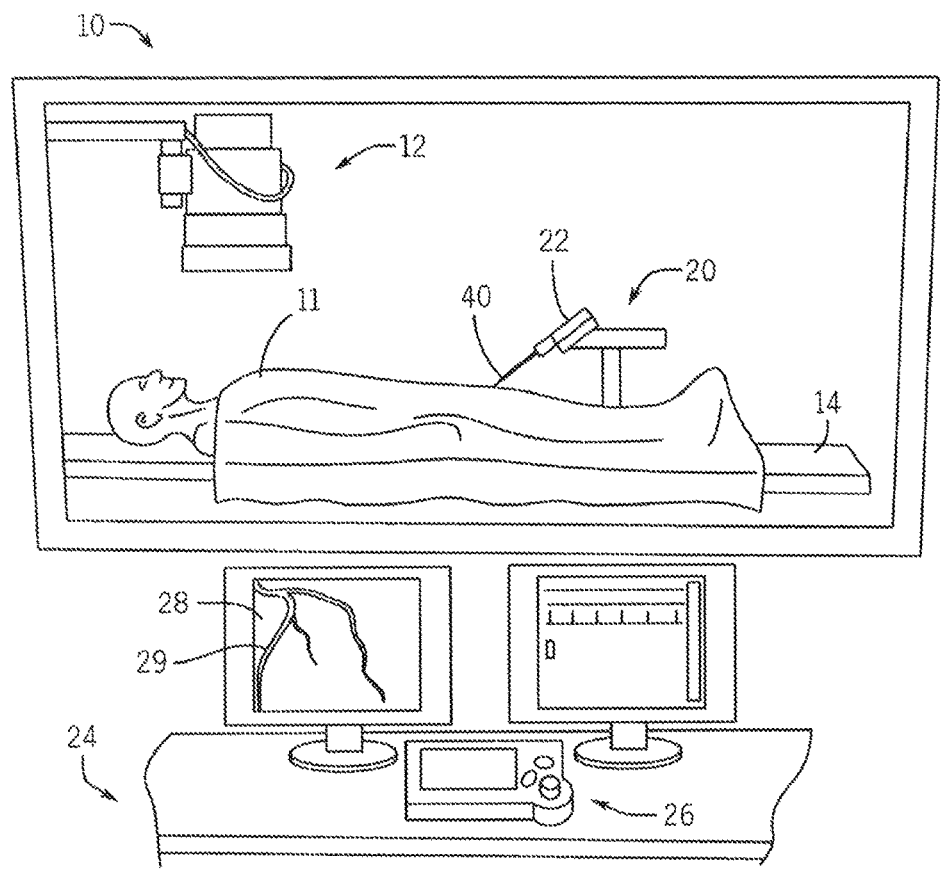
FIG. 1 is a schematic of the environment in which percutaneous interventional procedures are robotically performed.

FIG. 1 shows the environment in which the various embodiments of the present invention find particular utility. It shows a catheter laboratory 10 for robotically performing percutaneous interventional procedures. A patient 11 is supported on a table 14 and the procedure is observed with X-ray equipment 12. A cassette 22 supported by a robotic arm 20 is used to automatically feed a guide wire 30 (shown in FIG. 2) into a guide catheter 32 seated in an artery of the patient 11. The cassette 22 is controlled from a remote station 24 in order to isolate the medical personnel conducting the procedure from exposure to the X-ray radiation used to monitor the procedure by use of fluoroscopic equipment. The station includes remote controls 26 for controlling the cassette 22 and a screen 28 with which to monitor the progress of the procedure. It displays the arterial system 29 being addressed by the procedure. U.S. Pat. No. 7,887,549, incorporated herein by reference, has a detailed disclosure of this environment.

Figure 2:
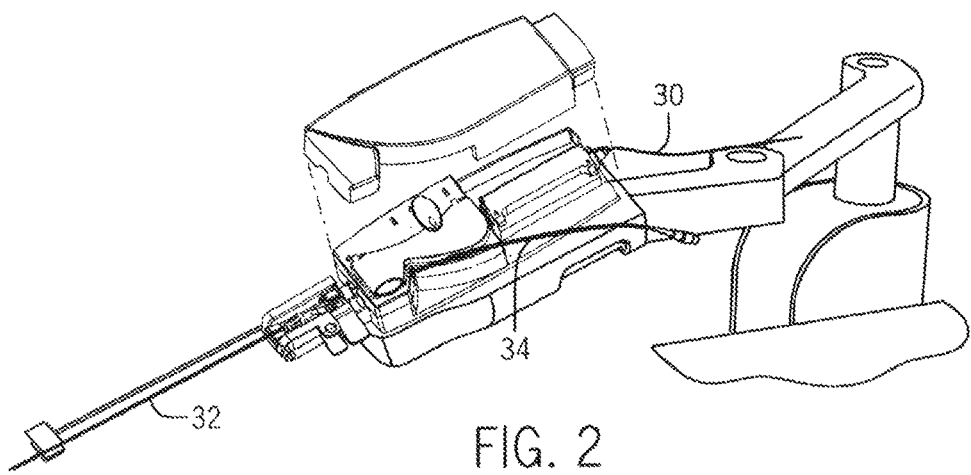
FIG. 2 is a schematic view of an FFR integration system and the robotic catheter system.

Referring to FIG. 2 cassette 22 drives guide wire 30 and/or a working catheter 34 such as a balloon and/or stent catheter through a guide catheter 32. A drive mechanism is housed in cassette 22 that provides translational and/or rotational movement to the guide wire and/or working catheter.

Figure 3:
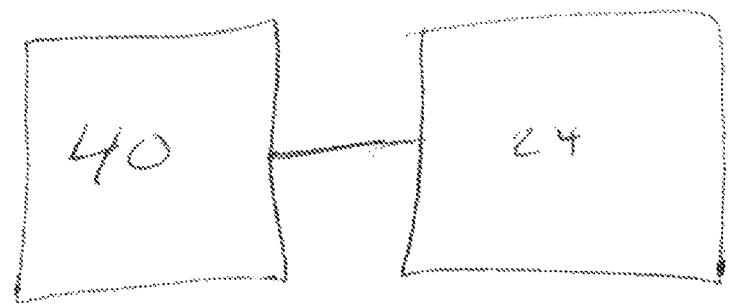
FIG. 3 is a schematic view of an integration system and a remote station.
Figure 4:
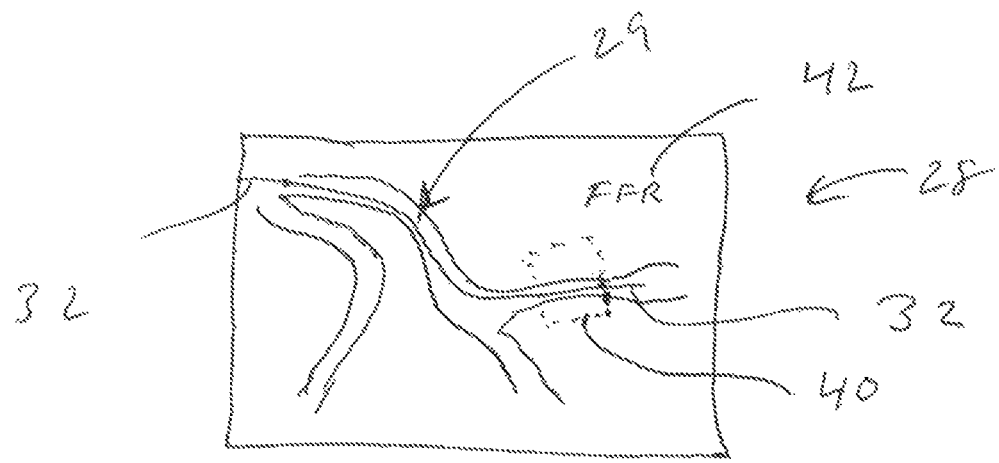
FIG. 4 is a schematic view of a display with an FFR value and identified region over which the FFR value represents.

Referring to FIG. 3 an integration system 40 is incorporated into remote station 24. In another embodiment integration system 40 is standalone system that communicates with remotes station 24 either wirelessly or through a wired connection such as a cable.

In one embodiment an integration system 40 receives data from a computer tomography (CT) system that includes CT scan data of a given patient. In one embodiment the CT scan data includes three dimensional data that provides a three dimensional array of the patient or a region of interest that is a portion of the patient anatomy of interest.

Integration system 40 using fractional flow reserve (FFR) technology can perform analysis on the CT data to determine areas within the vasculature of a patient that has reduced blood flow and/or reduced blood pressure. FFR technology is sued to identify pressure differences between various locations within a patient's vasculature. FFR is the ratio of maximum blood flow at one location to the normal maximum flow in the same vessel. Stated another way FFR=Pd/Pa where Pd=pressure distal to a lesion and Pa=normal pressure proximal to the lesion. The two points in which the pressure is identified is typically at a point before a stenosis lesion and after the stenosis lesion. In one embodiment FFR is provided as an absolute number representing the drop in blood pressure across a lesion.

In one implementation the information provided by FFR is used in conjunction with the graphical information provided during a percutaneous coronary intervention procedure. For example the graphical information of a vasculature that is obtained during a guide wire and/or a catheter procedure may be obtained by fluoroscopy or other known imaging systems and displayed in real time on a display for an operator. In one embodiment the FFR values for the region of interest are superimposed onto the graphical display of the vasculature region of interest to aid an operator in the placement of the stent utilizing the robotic catheter system. The region of interest is identified on the display and is superimposed by a graphic to indicate the region over which a FFR value has been obtained and calculated.

There are various methods for determining the FFR. In one method a pressure sensor is driven through a patient's vasculature on an elongated medical device. The pressure information can be conveyed back to the remote station 24. FFR values can be calculated based on points of interest identified by an operation of the robotic catheter system. The points may be identified by the use of an interface device such as a mouse by selecting two points on the display of the patient's vasculature. In one embodiment the blood pressure values are transmitted in real time so that the blood pressure is associated with a point in the vasculature which is stored within remote station 24.

In one implementation an elongated medical device 32 includes a proximal end and a distal end that is inserted into a vasculature of a patient. This device will be identified herein as the FFR Device. A pressure sensor is positioned proximate the distal free end of the FFR Device. The distal end is the end that is the free end in the vasculature, while the proximal end is the end opposite the distal end and outside of the vasculature when the distal end is within the vasculature.

Blood pressure values are obtained by the pressure sensor as the FFR Device is moved through the vasculature system. The blood pressure values are transmitted to an FFR processing station and the values are stored for further processing. Transmission of the blood pressure values from the blood pressure sensor in one implementation is electronically via a signal along the FFR Device. In another implementation, transmission of the data is done digitally either along the FFR Device or wirelessly.

The location of the distal end of the FFR Device is identified as a location within the vasculature by superimposing the location of the FFR Device blood pressure value with the location of the vasculature at the time the measurement was taken. An algorithm using the graphical display information obtained by an imaging system such as fluoroscopy associates the blood pressure value with a specific location in the vasculature. In one embodiment blood flow pressure information is transmitted continuously as the pressure sensor is moved through the vasculature. In one embodiment blood flow pressure information obtained from the pressure sensor is taken periodically based on a discrete movement of the FFR Device within the vasculature such that a pressure measurement is obtained every predetermined movement of the distal end of the FFR Device within the vasculature. In one embodiment the frequency of obtaining and transmitting blood pressure values is automatically revised based on the change of blood pressure from the previous readings. In this manner it is possible to identify the specific location of stenosis of interest. In one embodiment the change of blood pressure value of interest is set by an operator. As an example an operator may set a change of blood pressure of 5% that is a 5% reduction from a first location to a second location being at least a predetermined distance as way as being a value of interest. Once that threshold is identified, the frequency of measurements are increased over smaller distances so that the specific region of interest suggesting a stenosis or lesion is properly identified. It is also contemplated that once the threshold value is identified, the system automatically withdraws the FFR Device to the first location and obtains additional pressure readings as the FFR Device is once again moved forward or further into the vasculature of the patient. The operator may also set the change of blood pressure in terms of absolute pressure values and not as a percentage.

In one implementation a robotic linear drive mechanism 22 as disclosed in U.S. Pat. No. 7,887,549 linearly drives the distal end of the FFR Device into and out of the vasculature. The linear drive operates on a portion of the FFR Device intermediate the distal end and proximal end. In one implementation the robotic linear drive mechanism includes a rotational drive mechanism that operates to rotate the FFR Device along a longitudinal axis of the FFR Device. In one implementation a plurality of blood pressure value is obtained while the distal end of the FFR Device is in a fixed position within the vasculature. An average blood pressure value is determined by pressure measurements that are taken every fixed number of degrees. By example, in one embodiment the FFR Device is rotated 90 degrees four times and a blood pressure reading is obtained by a pressure sensor on the distal end of the FFR Device. The four readings are then averaged to obtain a blood pressure reading at a given location. The FFR Device is then moved an incremental linear unit and four additional pressure readings are obtained at 90 degree rotations of the FFR Device. It is contemplated that the number of readings and degree of rotation may be varied. It is also contemplated that at algorithm may be used to determine the appropriate blood pressure value based on the multiple pressure readings obtained at a given location.

In one embodiment, an algorithm identifies the likely region of a stenosis or lesion for operator analysis by use of a graphic superimposed on the display of the patient's vasculature illustrating the likely region of stenosis or legion. The length of the region of reduced blood pressure can aid in the operator in the selection of a proper sized stent to cover the area of interest.

In one embodiment a simulation module calculates the FFR values over a particular area of interest in the patient's vasculature. In one embodiment the simulation module determines an ideal location within the patient's vasculature to place a stent. In one embodiment the simulation module further determines one of or all of the type of stent, diameter of the stem, and length of the stent to optimize the FFR value after the stent has been placed within the patient's vasculature so that the blood flow post stent placement has been optimized.

In one implementation the FFR Device is incorporated into a balloon stent catheter such that a blood flow pressure reading is obtained as the balloon stent catheter is moved into position proximate a narrowing of the vasculature to be treated.

In one embodiment the integration module receives FFR values derived from a previously acquired CT scan of the patient in question. The FFR values are superimposed onto the x-ray views that are displayed on a display at the remote station. In one embodiment the FFR values are superimposed in real time as the x-ray images are acquired and displayed.

The simulation module via the use of an algorithm identifies the type and size of the stent required to maximize FFR readings post stent placement. In one embodiment the simulation module identifies the location for position of the stent based on FFR readings during real time of stent placement. The location for position of the stent can include a single point or can identify on the display the location that one end of the stent should be place before the stenosis and the location that the second end of the stent should be place beyond the stenosis.

In one embodiment the integration module includes a close loop navigation control based on the superimposed CT image and the real time X-ray tracking (or other tracking means) to optimize stent positioning using the robotic system. In one embodiment the position of the stent is verified to the pre acquired CT to make sure it provides the largest clinical outcome from this specific stent position. In one embodiment post deployment of the stent FFR measurements are made (invasive or through x-ray FFR) to verify flow and good clinical outcomes.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

What is claimed is:

1. A method comprising:
   obtaining a fractional flow reserve (FFR) value over a given distance in a patient's vasculature;
   providing a display of a region of interest of the patient's vasculature;
   displaying a graphic on the display of a location of the vasculature having a FFR value outside of a predetermined limit;
   robotically positioning a medical elongated device proximate the location; and
   obtaining the blood flow pressure at a given location within the vasculature including calculating an average blood flow pressure as a function of multiple blood flow pressure readings at different rotational orientation of the blood flow pressure sensor.

2. The method of claim 1, wherein the FFR value is defined as Pd/Pa where Pd is a first blood flow pressure at a first location within the vasculature and Pa is a second blood flow pressure at a second location within the vasculature.

3. The method of claim 2, wherein obtaining an FFR value includes obtaining the first blood flow pressure value with an FFR elongated medical device having a pressure sensor on a distal end thereof.

4. The method of claim 1, further including controlling the distance between blood flow pressure readings within a vasculature based on a predetermined algorithm.

5. A method comprising:
   obtaining a fractional flow reserve (FFR) value over a given distance in a patient's vasculature;
   providing a display of a region of interest of the patient's vasculature;
   displaying a graphic on the display of a location of the vasculature having a FFR value outside of a predetermined limit; and
   robotically positioning a medical elongated device proximate the location; and
   controlling the distance between blood flow pressure readings within a vasculature based on a predetermined algorithm;
   wherein the distance between blood flow pressure readings is determined automatically by a processor as a function of the rate of change of blood flow pressure per incremental unit travel within the vasculature.

6. The method of claim 3, further including robotically controlling the linear movement of the FFR elongated medical device with a robotically controlled drive mechanism.

7. A method comprising:
   obtaining a fractional flow reserve (FFR) value over a given distance in a patient's vasculature;
   providing a display of a region of interest of the patient's vasculature;
   displaying a graphic on the display of a location of the vasculature having a FFR value outside of a predetermined limit;
   robotically positioning a medical elongated device proximate the location;
   wherein the FFR value is defined as Pd/Pa where Pd is a first blood flow pressure at a first location within the vasculature and Pa is a second blood flow pressure at a second location within the vasculature;
   wherein obtaining an FFR value includes obtaining the first blood flow pressure value with an FFR elongated medical device having a pressure sensor on a distal end thereof;
   robotically controlling the linear movement of the FFR elongated medical device with a robotically controlled drive mechanism; and
   further including robotically controlling the rotational movement of the FFR elongated medical device with the robotically controlled drive mechanism.

8. The method of claim 6, further including automatically withdrawing the distal end of the FFR elongated medical device a distance within the vasculature and reinserting the FFR elongated medical device and robotically controlling the linear movement of the FFR elongated medical device with a robotically controlled drive mechanism.

9. The method of claim 1, wherein the FFR values are obtained from a computerized tomography (CT) scan.

10. The method of claim 1, wherein the FFR values are obtained with an elongated medical device having a pressure sensor on a distal end thereof.

11. The method of claim 10, further including a processor identifying a region of stenosis as a function of FFR values within the vasculature.

12. The method of claim 5 wherein the frequency of obtaining and transmitting blood pressure values is automatically revised based on the change of blood pressure from the previous readings.

13. A method comprising:
   obtaining a fractional flow reserve (FFR) value over a given distance in a patient's vasculature;
   providing a display of a region of interest of the patient's vasculature;
   displaying a graphic on the display of a location of the vasculature having a FFR value outside of a predetermined limit;
   robotically positioning a medical elongated device proximate the location;
   wherein the FFR value is defined as Pd/Pa where Pd is a first blood flow pressure at a first location within the vasculature and Pa is a second blood flow pressure at a second location within the vasculature; and
   setting a change in blood pressure value of interest and automatically increasing the frequency of measurements over smaller distances and identifying a specific region of interest suggesting a stenosis or lesion is identified based on the FFR values.

14. The method of claim 12, wherein once a threshold FFR value is identified further including automatically withdrawing the FFR elongated medical device to the first location and obtaining additional pressure readings as the FFR elongated medical device moved forward into the vasculature of the patient with increased frequency of measurements.

15. The method of claim 13 wherein obtaining the blood flow pressure values at a given location within the vasculature includes calculating a blood flow pressure as a function of multiple blood flow pressure readings at different rotational orientations of the FFR elongated medical device.

16. The method of claim 15 wherein the FFR elongated medical device is rotated by a rotational drive mechanism along a longitudinal axis of the FFR elongated medical device.

17. The method of claim 16 wherein an average blood pressure value is determined from the plurality of blood pressure values obtained at the fixed position algorithm is used to determine the blood pressure value based on the multiple pressure readings obtained at a given location.

18. The method of claim 16, wherein the FFR elongated medical device is then moved an incremental linear unit by a linear drive mechanism and additional pressure readings are obtained at different degrees of rotations.

19. The method of claim 15 an algorithm identifies the likely region of a stenosis or lesion for operator analysis by use of a graphic superimposed on the display of the patient's vasculature illustrating the likely region of stenosis or legion.

\* \* \* \* \*